United States Patent
Poeze et al.

(10) Patent No.: US 9,936,917 B2
(45) Date of Patent: Apr. 10, 2018

(54) PATIENT MONITOR PLACEMENT INDICATOR

(71) Applicant: Cercacor Laboratories, Inc., Irvine, CA (US)

(72) Inventors: Jeroen Poeze, Mission Viejo, CA (US); Marcelo M. Lamego, Coto De Caza, CA (US)

(73) Assignee: MASIMO LABORATORIES, INC., Irvine, CA (US)

( * ) Notice: Subject to any disclaimer, the term of this patent is extended or adjusted under 35 U.S.C. 154(b) by 1000 days.

(21) Appl. No.: 14/209,844

(22) Filed: Mar. 13, 2014

(65) Prior Publication Data
US 2014/0275808 A1   Sep. 18, 2014

Related U.S. Application Data

(60) Provisional application No. 61/785,180, filed on Mar. 14, 2013.

(51) Int. Cl.
G08B 21/00      (2006.01)
A61B 5/00       (2006.01)
A61B 5/1455     (2006.01)

(52) U.S. Cl.
CPC .......... *A61B 5/684* (2013.01); *A61B 5/14551* (2013.01); *A61B 5/6826* (2013.01); *A61B 5/742* (2013.01); *A61B 5/743* (2013.01); *A61B 5/7405* (2013.01)

(58) Field of Classification Search
CPC ... A61B 5/1071; A61B 5/6843; A61B 5/1118; A61B 5/1127; A61B 5/14551; A61B 5/149; A61B 5/14532; A61B 5/14552; A61B 5/061; A61B 5/06
USPC ....... 600/595, 322, 407, 323, 331, 310, 316, 600/424, 300; 340/573.1, 4.43, 635, 340/686.1
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |

(Continued)

*Primary Examiner* — Hoi Lau
(74) *Attorney, Agent, or Firm* — Knobbe, Martens, Olson & Bear, LLP

(57) ABSTRACT

A monitoring device for measuring one or more physiological parameters of a medical patient can include a finger clip sensor connected to a monitor. A placement indicator helps the patient to properly position the sensor. The monitor can display a message alerting the patient to reposition the sensor. The device can delay measurement until the sensor is properly positioned.

25 Claims, 5 Drawing Sheets

(56) References Cited

U.S. PATENT DOCUMENTS

| | | |
|---|---|---|
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,961,474 A * | 10/1999 | Reis ............... A61B 5/1071 600/595 |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 * | 2/2003 | Kiani ............... A61B 5/6843 600/322 |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |

(56) References Cited

U.S. PATENT DOCUMENTS

| | | |
|---|---|---|
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,130 B2 * | 3/2011 | Raridan, Jr. ........ A61B 5/14552 600/323 |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |

(56) References Cited

U.S. PATENT DOCUMENTS

| | | |
|---|---|---|
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 * | 1/2013 | Lamego ............... A61B 5/061 600/322 |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 * | 3/2013 | Kiani ............... A61B 5/061 600/310 |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 * | 4/2014 | Kiani ............... A61B 5/061 600/310 |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 * | 6/2014 | Poeze ............... A61B 5/14551 340/3.43 |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 * | 6/2014 | Lamego ............... A61B 5/061 600/322 |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |

(56) References Cited

U.S. PATENT DOCUMENTS

| | | |
|---|---|---|
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 2004/0189475 A1* | 9/2004 | Cooper ............... A61B 5/1118 340/573.1 |
| 2005/0245807 A1* | 11/2005 | Boese ................. A61B 5/1127 600/407 |
| 2006/0161054 A1 | 7/2006 | Reuss et al. |
| 2007/0129616 A1* | 6/2007 | Rantala .............. A61B 5/14551 600/323 |
| 2007/0282478 A1 | 12/2007 | Al-Ali et al. |
| 2009/0076354 A1* | 3/2009 | Huiku ................. A61B 5/1495 600/331 |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1* | 1/2010 | Vo ...................... A61B 5/14532 600/310 |
| 2010/0030040 A1* | 2/2010 | Poeze ................. A61B 5/14532 600/316 |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2014/0005531 A1* | 1/2014 | Taylor .................. A61B 5/06 600/424 |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |

(56) References Cited

U.S. PATENT DOCUMENTS

| | | |
|---|---|---|
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1* | 9/2014 | Poeze .............. A61B 5/14551 600/300 |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0296664 A1* | 10/2014 | Bruinsma ............ A61B 5/0059 600/310 |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0360054 A1* | 12/2015 | Jeong .................. A61N 5/1049 600/1 |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |

\* cited by examiner

PATIENT MONITOR PLACEMENT INDICATOR

RELATED APPLICATIONS

Incorporation by Reference to any Priority Applications

Any and all applications for which a foreign or domestic priority claim is identified in the Application Data Sheet as filed with the present application are incorporated by reference under 37 CFR 1.57 and made a part of this specification.

BACKGROUND

Field of the Disclosure

The disclosure herein relates generally to patient monitoring with non-invasive physiological sensors. More specifically, the present disclosure relates to devices and methods for aiding a patient in positioning the physiological sensor for more accurate results.

Description of the Related Art

The standard of care in caregiver environments includes patient monitoring through spectroscopic analysis using, for example, a pulse oximeter. Devices capable of spectroscopic analysis generally include a light source(s) transmitting optical radiation into or reflecting off a measurement site, such as, body tissue carrying pulsing blood. After attenuation by tissue and fluids of the measurement site, a photo-detection device(s) detects the attenuated light and outputs a detector signal(s) responsive to the detected attenuated light. A signal processing device(s) process the detector(s) signal(s) and outputs a measurement indicative of a blood constituent of interest, such as glucose, oxygen, met hemoglobin, total hemoglobin, other physiological parameters, or other data or combinations of data useful in determining a state or trend of wellness of a patient.

In noninvasive devices and methods, a sensor is often adapted to position a finger proximate the light source and light detector. For example, noninvasive sensors often include a clothespin-shaped housing that includes a contoured bed conforming generally to the shape of a finger. The contoured bed can help position and stabilize the finger for measurement.

SUMMARY

This disclosure describes embodiments of noninvasive methods, devices and systems for measuring physiologically relevant patient characteristics and for determining proper positioning of the physiological sensor for a specific patient. The monitoring device can determine a reference position of the sensor with respect to the patient when the sensor is properly positioned on the patient. After the reference position is determined, the monitoring device can use the reference position to help the patient maintain the position of the sensor in the appropriate position for clear and accurate measurements. In certain embodiments, when the device detects improper positioning, a display on a monitor alerts or provides an indication to the patient that the sensor is out of position. In some embodiments, the monitoring device can delay taking measurements until the sensor is returned to the reference position. In some embodiments, the display on a monitor associated with the sensor displays an interactive game for the patient to play, which can help the patient position the monitoring device.

For purposes of summarizing the disclosure, certain aspects, advantages and novel features have been described herein. It is to be understood that not necessarily all such advantages can be achieved in accordance with any particular embodiment disclosed herein. Thus, the disclosure described herein can be embodied or carried out in a manner that achieves or optimizes one advantage or a group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments described herein and not to limit the scope thereof.

DETAILED DESCRIPTION OF PREFERRED EMBODIMENTS

A monitoring device in accordance with one embodiment of the present disclosure comprises a physiological sensor including a detector housing for attachment to a measurement site. The measurement site can be, for example, a patient's finger, and the detector housing can comprise a clothespin-shaped housing that includes a contoured bed conforming generally to the shape of a finger. The monitoring device further comprises one or more monitors that process and/or display the sensor's output and/or other information. The monitors can include various components, such as a sensor front end, a signal processor, a display, etc.

The sensor can be integrated with a monitor, for example, into a handheld unit including the sensor, a display and user controls. In other embodiments, the physiological sensor can be connected to and communicate with the monitor(s) via a cable or a wireless connection. The communication can be via wire(s), cable(s), flex circuit(s), wireless technologies, or other suitable analog or digital communication methodologies and devices to perform those methodologies. Many arrangements allow the sensor to be attached to the measurement site while the monitor is attached elsewhere on a patient, such as the patient's arm, placed at a location near the patient, such as a bed, shelf or table, or held by the patient.

Reference will now be made to the Figures to discuss embodiments of the present disclosure.

Figure 1:
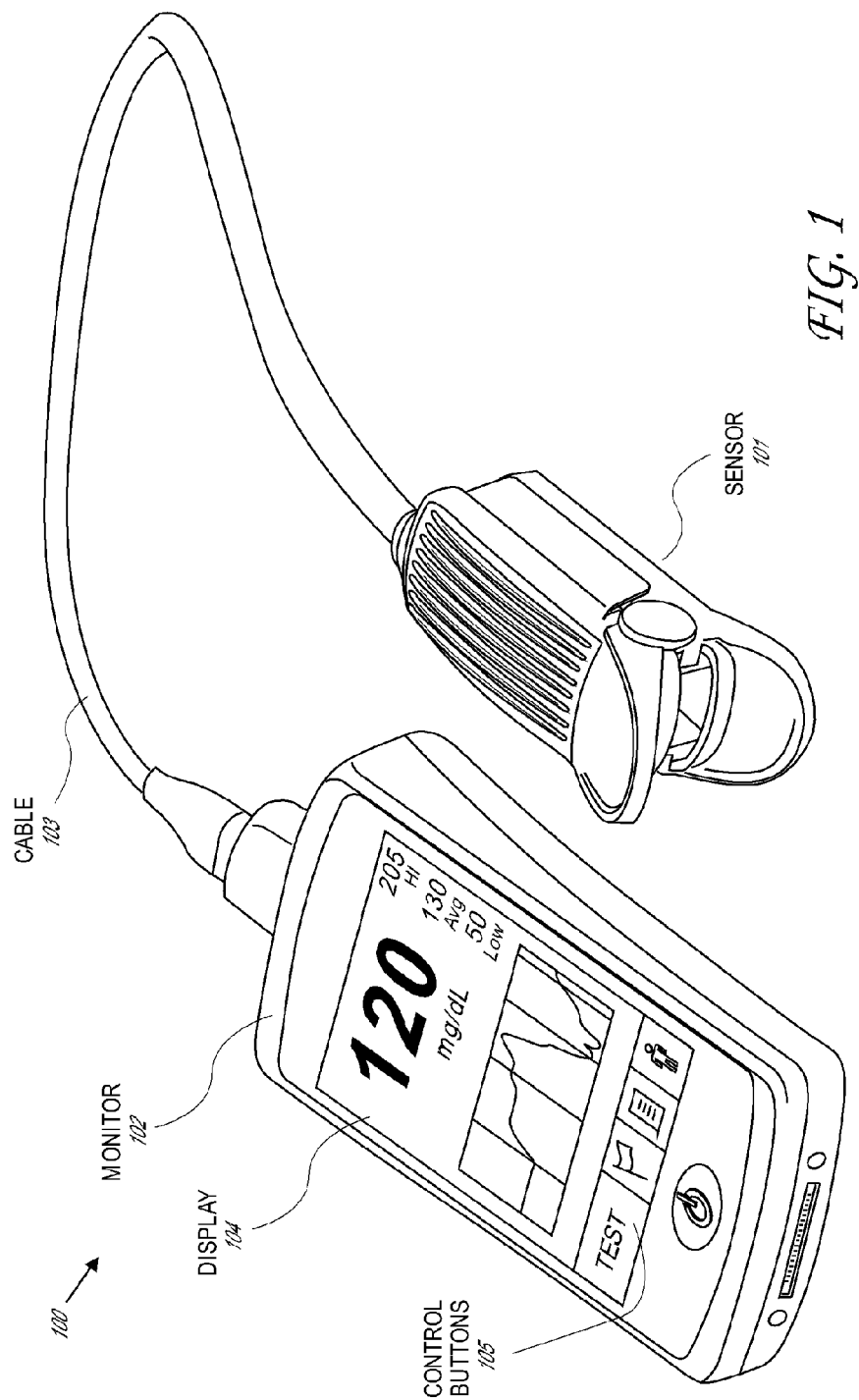
FIG. 1 illustrates an exemplary handheld monitor and an exemplary noninvasive optical sensor of a patient monitoring system, according to embodiments of the disclosure.

FIG. 1 illustrates one example of a monitoring device 100. In the depicted embodiment, the monitoring device 100 includes a finger clip sensor 101 connected to a monitor 102 via a cable 103. In the embodiment shown, the monitor 102 includes a display 104, control buttons 105 and a power button. Moreover, the monitor 102 can advantageously include electronic processing, signal processing, and data storage devices capable of receiving signal data from said sensor 101, processing the signal data to determine one or more output measurement values indicative of one or more physiological parameters of a monitored patient, and displaying the measurement values, trends of the measurement values, combinations of measurement values, and the like. The electronic processing, signal processing, and data storage devices of the monitor 102 can also be capable of receiving data, processing the data, generating displays based at least in part on the data as further described below, and directing the system when to record measurements of the physiological parameters of interest.

The cable 103 connecting the sensor 101 and the monitor 102 can be implemented using one or more wires, optical fiber, flex circuits, or the like. In some embodiments, the cable 103 can employ twisted pairs of conductors in order to minimize or reduce cross-talk of data transmitted from the sensor 101 to the monitor 102. Various lengths of the cable 103 can be employed to allow for separation between the sensor 101 and the monitor 102. The cable 103 can be fitted with a connector (male or female) on either end of the cable 103 so that the sensor 101 and the monitor 102 can be connected and disconnected from each other. Alternatively, the sensor 101 and the monitor 102 can be coupled together via a wireless communication link, such as an infrared link, radio frequency channel, or any other wireless communication protocol and channel.

The monitor 102 can be attached to the patient. For example, the monitor 102 can include a belt clip or straps that facilitate attachment to a patient's belt, arm, leg or the like. The monitor 102 can also include a fitting, slot, magnet, LEMO snap-click connector or other connecting mechanism to allow the cable 103 and sensor 101 to be attached to the monitor 102.

The monitor 102 can also include other components, such as a speaker, power button, removable storage or memory (e.g., a flash card slot), an AC power port, and one or more network interfaces, such as a universal serial bus interface or an Ethernet port. For example, the monitor 102 can include a display 104 that can indicate measurements obtained by the physiological sensor, prompt a user for input, or display messages and/or games as discussed below.

In addition, although a single sensor 101 with a single monitor 102 is shown, different combinations of sensors and device pairings can be implemented. For example, multiple sensors can be provided for a plurality of differing patient types or measurement sites or even patient fingers.

Example monitoring devices are described in U.S. Publication No. 2010/0030040, filed Aug. 3, 2009, titled "Multi-Stream Data Collection System for Noninvasive Measurement of Blood Constituents" and U.S. Publication No. 2010/0010326, filed Jul. 2, 2009, titled "Contoured Protrusion for Improving Spectroscopic Measurement of Blood Constituents," the disclosures of which are both hereby incorporated by reference in their entirety. An example commercial embodiment of a monitoring device is available from Masimo® Corporation of Irvine, Calif.

Figure 2:
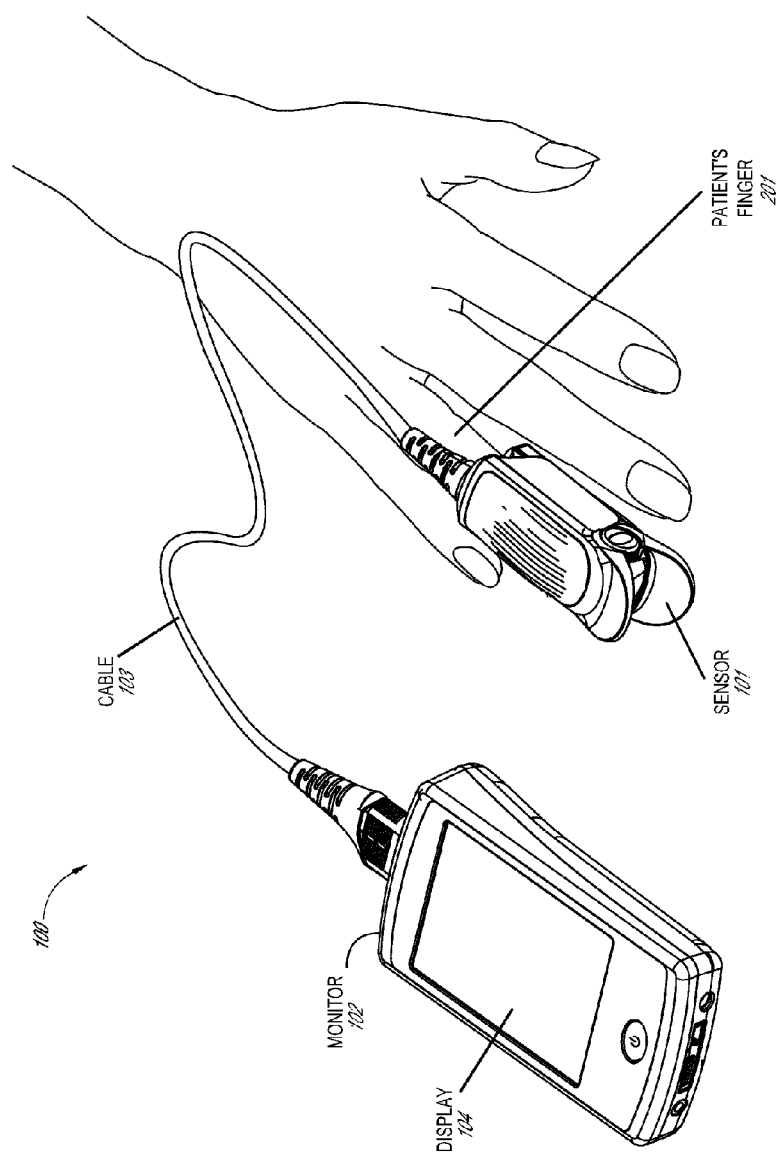
FIG. 2 illustrates a monitoring device in accordance with one embodiment with the sensor attached to a patient's finger.

FIG. 2 shows a monitoring device 100 in accordance with one embodiment of the present disclosure with the sensor attached to a patient's finger 201. The patient' finger 201 has a range of movement within the sensor 101. The patient's finger 201 can move in all directions, such as longitudinally, vertically, and from horizontally. When the patient's finger 201 is not correctly positioned with the sensor 101, the sensor 101 can provide erroneous data.

Figure 4:
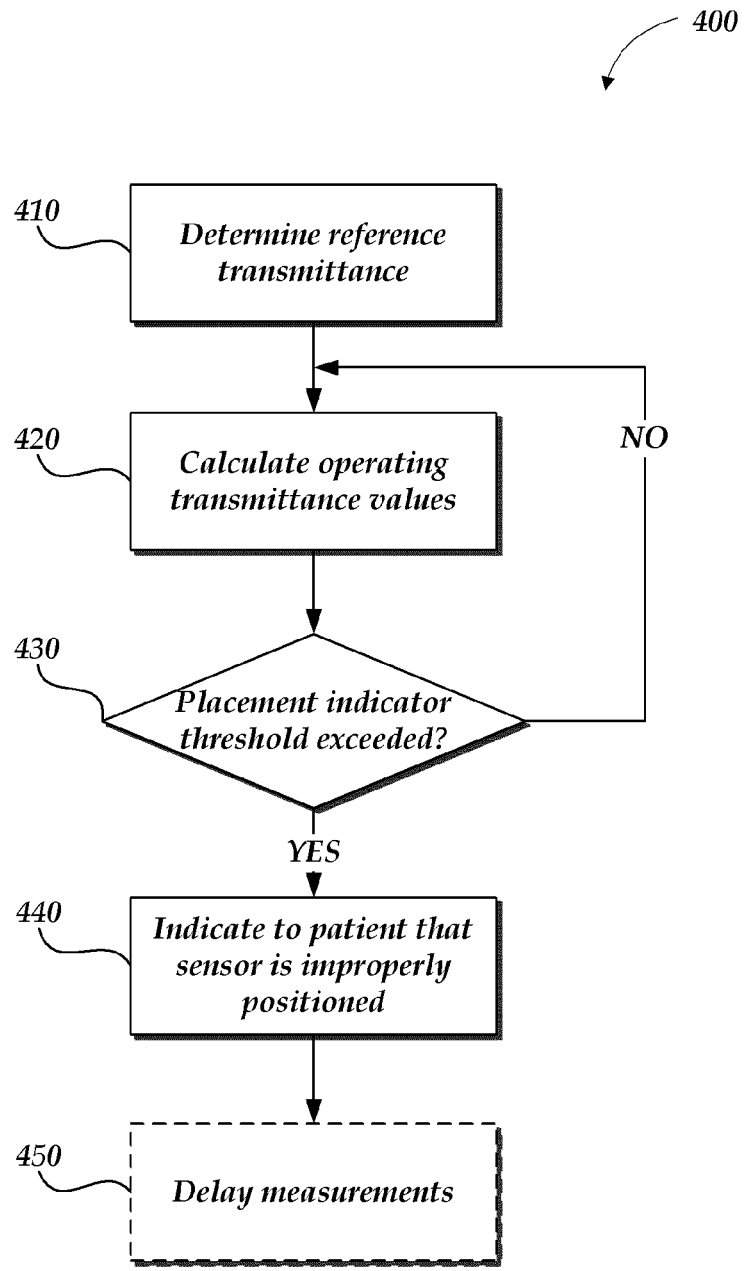
FIG. 4 illustrates an embodiment of a flowchart for operation of the monitoring system utilizing sensor placement indication

Before attaching the physiological sensor 101 to the patient and beginning monitoring, a user can input information regarding the patient, e.g., whether the patient is an adult or child, into the monitor 102 via, for example, control buttons 105 on the monitor housing or touch screen display buttons 305 (shown in FIG. 4). In some embodiments, the system displays a message on the display 104 prompting the user to input such information regarding the patient or type of display desired.

When the sensor 101 is placed on the patient's finger 201, the monitor 102 determines a reference position for the sensor 101. A patient's finger is used in this illustrative example, however, the principles discussed herein can apply equally to a sensor being positioned on any measurement site of a patient. The reference position is first determined after the sensor 101 has been properly positioned on the patient's finger 201. A user, such as a caregiver, can help correctly position the sensor 101 on the patient's finger. In order to set the reference position the user can provide an indication (e.g., pushing a button) to the monitor 102 to store the current position as the reference position. The monitor 102 determines the reference position by calculating at least one reference transmittance value based on the positioning of the physiological sensor 101. The reference transmittance values can be stored in nonvolatile storage within the monitor 102. In some embodiments, multiple sets of reference transmittance values can be stored.

The reference position stored by the monitor 102 is subsequently used by the monitor 102 to determine whether the patient's finger 201 is properly positioned within the sensor 101. The monitor 102 can continuously monitor the position of the patient's finger 201 to determine whether it is correctly positioned within the sensor. In some embodiments, when the monitor 102 detects that the patient's finger is not properly positioned within the sensor 101 for accurate measurements, the monitor 102 can delay processing measurements and trigger an appropriate display on the display 104 indicating that the sensor 101 needs to be repositioned. In some embodiments, the monitor 102 can detect the direction and the magnitude of the improper positioning of the sensor 101. The display 104 can provide an indication directing the patient how to adjust the sensor 101 for more accurate measurements, for example, directing the patient to move the sensor 101 longitudinally. The system can continue to provide one or more indications until the sensor 101 is properly positioned by the patient. This feature can help alert the patient that the physiological sensor 101 is positioned incorrectly and needs to be readjusted. The monitor can use the reference position to provide instructions to the patient for positioning the physiological sensor without the aid of a medical practitioner. This can help reduce erroneous measurements caused by improper positioning of the physiological sensor.

Figure 3:
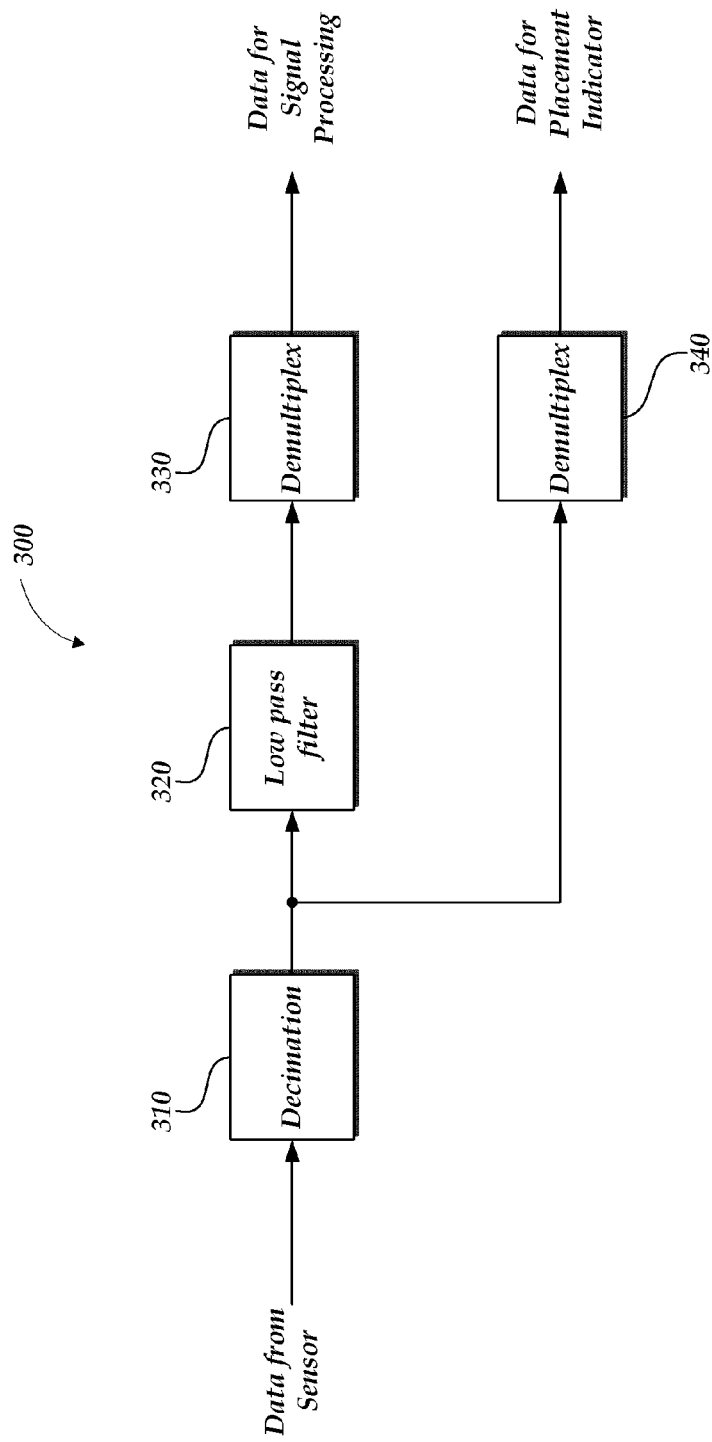
FIG. 3 illustrates a block diagram illustrating data processing of signals used for placement indication.

FIG. 3 is a block diagram illustrating a decimation process 300 for signals received from a physiological sensor 101. At block 310, the signal data received from the sensor 101 undergoes a first stage decimation. The first stage decimation can be performed on batches of signal data based on the size of an averaging window. After the first stage decimation at block 310, the signal data can be filtered at block 320 or sent to a demultiplexer at block 340. At block 320, the signal data is filtered using a low pass filter and then sent to a demultiplexer at block 330. The filtered signal data is used by the monitor 102 to perform additional signal processing steps in order to process the physiological signals based on the filtered signal data.

Signal data for the placement indication algorithm is taken after the first stage decimation process and does not undergo filtering through the low pass filter at block 320. The signal data for the placement indicator bypasses the low pass filter 320 and is demultiplexed at block 340. The low pass filter adds additional processing time. By bypassing the low pass filter and using the unfiltered data for the placement indicator, the patient can receive indications that the sensor 101 is not properly positioned more frequently. In some embodiments the patient can receive positioning updates one or more times every second, whereas, filtering the signal data can require one or more seconds of additional processing. The additional time that is required to filter the signal data increases propagation delay and decreases responsiveness of the placement indicator, which can make it difficult for the patient to adjust the sensor in real-time. The signal data does not need to be filtered to calculate placement indication. The signal data that is being used for placement indication does not need to be as high quality as the data that is used to derive the physiological measurements. By using the signal data that has not been processed by the low pass filter reduces propagation delay and improves responsiveness of the placement indicator.

The signal data is used to calculate at least one reference transmittance value in order to determine the reference position. The reference transmittance values are calculated and stored in non-volatile storage. The reference transmittance values in the placement indicator algorithm are compared with the operating transmittance values. The difference between the reference transmittance values and the operating transmittance values, as calculated, can be used as an indicator for placement. The closer the placement indicator is to zero, the closer the finger placement is to the finger placement when the reference transmittance values were acquired. The system can process the operating transmittance values in an open loop, so that the most current value is continuously being recalculated.

A reference transmittance value can be calculated for each LED and channel combination that is being used to determine the placement indication. In some embodiments, all of the LEDs and channels are used to determine placement indication. In some embodiments a subset of the total number of LEDs and channels are used to determine placement indication. In some embodiments, wavelengths that experience high levels of scattering are not used for placement indication.

The value for transmittance for each LED and channel combination is calculated using the following equation:

$$T = \frac{DC}{power \times PGA_{gain}} \quad \text{Eq. 1}$$

T=transmittance
DC=measured DC intensity
power=estimated LED power based on current and temperature
$PGA_{gain}$=gain setting of programmable gain amplifier A transmittance value is calculated using the DC components of the signals. The power is based on the current and the temperature when the measurement is taken. The power compensates for changes in current and temperature in the operating transmittance values that are different from the values of current and temperature used to calculate the reference transmittance values. The monitor can have a transmittance calculator to calculate the transmittance value.

The reference transmittance values and operating transmittance values for each LED and channel combination is used in the following equation to determine a placement indication.

$$P = -\sum_{i=1}^{n} \left| \frac{T_i' - T_i}{T_i'} \right| \quad \text{Eq. 2}$$

$$IF \sum_{i=1}^{n} \frac{T_i' - T_i}{T_i'} < 0,$$

$$P = \sum_{i=1}^{n} \left| \frac{T_i' - T_i}{T_i'} \right| \text{ otherwise.}$$

$T_i$=measured transmittance for channel/LED
$T_i'$=reference transmittance for channel/LED
n=number of LEDs times the number of channels
P=placement indication Ideally, the calculated value of the placement indication, P, would be zero. As the value of the equation approaches zero, the position of the physiological sensor is closer to the reference position. The value of the placement indicator can be positive or negative. The calculated value of the placement indicator provides a magnitude of difference in positioning between the reference position and the current position of the patient's finger. As the finger is moved closer to the correct positioning, the value of the placement indicator will approach zero. The value of the placement indicator does not provide an absolute unit of measurement. Rather, the value is reduced as the finger approaches the reference position and increased as the finger moves away from the reference position. In some embodiments, the sensor can extrapolate direction based on the positive and negative values associated with the placement indicator value. As such, the system may be able to provide a visual indication to the patient of the approximate direction that the finger needs to be moved within the sensor to substantially align the position of the finger with the reference position. The current position of the finger can be different that the reference position in any direction (e.g., horizontally, vertically, longitudinally, etc.). The monitor can have a placement indication calculator to calculate the placement indication.

Generally, the value of the placement indication will not be zero. Rather than have the patient constantly adjusting the position of the sensor, the monitoring system can have a placement indication threshold. The placement indication threshold is used to determine whether the finger is within an acceptable measurement tolerance. When the placement indication threshold is exceeded then the monitoring system can indicate to the patient that the sensor is not properly positioned.

FIG. 4 illustrates a flowchart for operation of the monitoring system utilizing sensor placement indication 400. At block 410 reference transmittance values are determined. In some embodiments, the reference transmittance values can be determined based on all of the available signals from the sensor. In some embodiments, the reference transmittance is based on a subset of signals from the sensor. The reference transmittance value can be stored in the monitoring system.

At block 420, the current operating transmittance values are calculated using the transmittance algorithm. The monitoring system can continuously calculate and update the transmittance values so that the patient has an updated value of the position of the sensor at regular intervals. In some embodiments, the transmittance values can be updated periodically, such as multiple times a second. In some embodiments, the transmittance values can be are updated at less frequent intervals. In some embodiments, the transmittance values are updated more frequently.

At block 430, the placement indicator algorithm is used to determine the placement indicator transmittance value. The placement indicator transmittance value is compared to a threshold value. If the placement indicator transmittance value is greater than the threshold value then the process proceeds to block 440. If the placement indicator transmittance value is less than the threshold value the monitoring system returns to block 420 and continues to calculate the operating transmittance values. The monitoring system can continue to calculate the operating transmittance values for as long as the sensor is in use by the patient.

At block 440, the monitoring system can indicate to the patient on a display of the monitor that the sensor is improperly positioned. In some embodiments, the indication to the patient can be an alarm that gets the attention of the patient, such as an audible sound. In some embodiments, the indication can provide a message to the patient that the sensor is improperly positioned. The message can provide text, numeric values and/or other visual cues that can help the patient to reposition the sensor. For example, as the patient repositions the sensor, the display can display arrows that help the patient reposition the patient reposition the sensor. In some embodiments, the indication can be an interactive indicator, such as a game, that is displayed and can help the patient reposition the sensor so that it is correctly positioned on the patient's finger. Games or other interactive displays can be beneficial in instructing pediatric patients that may have difficulty interpreting a textual or other indication. An embodiment of an interactive indicator is further illustrated with reference to FIG. 5.

At block 450, the monitoring system can optionally delay measurements until the placement indicator transmittance value is below the threshold. In some embodiments, the monitoring system may continue to determine measurements even though the placement indicator threshold has been exceeded.

Figure 5:
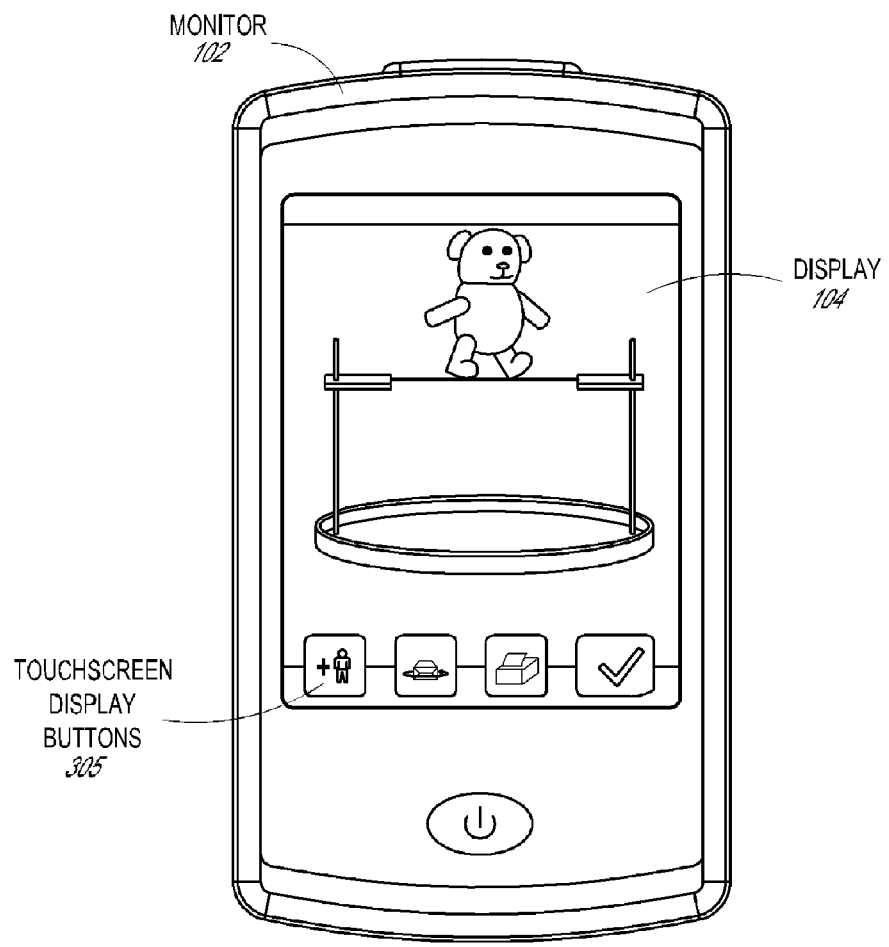
FIG. 5 illustrates an exemplary embodiment of an interactive game displayed on a monitor associated with a physiological sensor according to embodiments of the disclosure.

In one embodiment illustrated in FIG. 5, the display 104 displays and initiates an interactive indicator, such as a movement or balance game rather than another type of indication, such as a textual, verbal, or symbolic indicator, in response to the detection of inappropriate positioning. A young child may not be able to read a message directing him or her to adjust the physiological sensor. Even if the child could read such a message, children often have difficulty remaining still even if asked or directed to do so. In certain embodiments, the display 104 is configured to display one or more games such that the patient is motivated by the game to move the physiological sensor to the appropriate position. In addition to helping the patient adjust the monitoring device in order to obtain accurate readings, such games can advantageously provide an activity to occupy and possibly distract the patient.

In one embodiment, the game display comprises images of a teddy bear on a tightrope. Movement of the patient's finger and therefore the sensor corresponds to and causes movement of the bear. The game can provide indications of the direction that the patient needs to move the finger in order to move the bear to the proper position on the tightrope. In other similar embodiments, the bear can be replaced by an animal or human and the tightrope can be replaced by a balance beam, among other things.

One or more indicators, such as interactive indicators (e.g., games) disclosed above, similar interactive indicators, or other indicators can be stored in the monitor's 102 data storage device. Additional games can be loaded to the monitor via a removable storage or memory (e.g., a flash card) or a network interface.

After a user provides input to the monitor 102 indicating that the patient is a child or that a game is to be used rather than a verbal alert message, the display 104 can provide various game options available and prompt the user or patient to select one via a touch screen display or control buttons 105.

While a number of preferred embodiments and variations thereof have been described in detail, other modifications and methods of using and medical applications for the same will be apparent to those of skill in the art. Accordingly, it should be understood that various applications, modifications and substitutions can be made of equivalents without departing from the spirit of the disclosure or the scope of the claims.

What is claimed is:

1. A noninvasive medical monitoring device, said monitoring device comprising:
    a physiological sensor configured to output at least one physiological signal; and
    a monitor comprising a display and a signal processing system comprising;
        a transmittance calculator configured to:
            calculate at least one reference transmittance value from said at least one physiological signal, wherein said at least one reference transmittance value is indicative of a reference position of said physiological sensor on a measurement site of a patient, and
            calculate at least one operating transmittance value from said at least one physiological signal, wherein said at least one operating transmittance value is indicative of a position of said physiological sensor on said measurement site of said patient;
        a placement indication calculator configured to calculate a placement indication value based, at least in part, on said at least one reference transmittance value and said at least one operating transmittance value, wherein said placement indication value is indicative of said position of said physiological sensor on said measurement site relative to said reference position; and
        a processing module configured to determine whether said placement indication value exceeds a placement indication threshold.

2. The noninvasive medical monitoring device of claim 1, wherein said processing module is further configured to generate an output on said display based at least in part on said placement indication value.

3. The noninvasive medical monitoring device of claim 2, wherein said output comprises one or more verbal messages.

4. The noninvasive medical monitoring device of claim 2, wherein said output comprises a movement or balance game.

5. The noninvasive medical monitoring device of claim 1 further comprises a data storage device configured to store said at least one reference transmittance value.

6. The noninvasive medical monitoring device of claim 1, wherein said transmittance calculator is configured to calculate said at least one reference transmittance value based on an input received from a user.

7. The noninvasive medical monitoring device of claim 1, wherein said transmittance calculator is configured to calculate said at least one operating transmittance value periodically.

8. The noninvasive medical monitoring device of claim 1, wherein said transmittance calculator is configured to calculate said at least one operating transmittance value prior to filtering said at least one physiological signal with a low pass filter.

9. The noninvasive medical monitoring device of claim 2, wherein said output indicates a magnitude and a direction of said position relative to said reference position.

10. A method of determining positioning of a sensor, said method comprising:
 calculating at least one reference transmittance value from a first plurality of physiological signals received from a sensor on a measurement site of a patient, wherein said at least one reference transmittance value is indicative of a reference position of said sensor on said measurement site;
 calculating at least one operating transmittance value from a second plurality of physiological signals received from said sensor, wherein said at least one operating transmittance value is indicative of a current position of said sensor on said measurement site;
 calculating a placement indication value based, at least in part, on said at least one reference transmittance value and said at least one operating transmittance value;
 determining whether said placement indication value exceeds a placement indicator threshold; and
 generating an output on a display based at least in part on said placement indication value when said placement indication value exceeds said placement indicator threshold.

11. The method of claim 10, wherein said output comprises an indicator for notifying said patient that said sensor is incorrectly positioned.

12. The method of claim 11, wherein said indicator is an audible indicator.

13. The method of claim 11, wherein said indicator is a visual indicator.

14. The method of claim 11, wherein said indicator comprises at least one of a direction or a magnitude.

15. The method of claim 10 further comprising receiving an input to calculate said at least one reference transmittance value.

16. The method of claim 10 further comprising delaying determining a physiological measurement associated with at least one physiological signal when said placement indicator value exceeds said placement indicator threshold.

17. A method of determining positioning of a sensor on a measurement site of a patient, said method comprising:
 calculating a first value from a first set of physiological signal data received from said sensor, wherein said first value is indicative of a first position of said sensor on said measurement site;
 calculating a second value from a second set of physiological signal data received from said sensor after calculating said first value, wherein said second value is indicative of a second position of said sensor on said measurement site;
 comparing said first value and said second value; and
 generating an indicator on a monitor based at least in part on said comparison between said first value and said second value.

18. The method of claim 17, wherein said indicator notifies said patient that said sensor is incorrectly positioned.

19. The method of claim 17, wherein said indicator is at least one of an audible indicator or a visual indicator.

20. The method of claim 17 further comprising receiving an input from a user prior to initiating calculating said first value.

21. The method of claim 17, wherein calculating said second value occurs at regular intervals.

22. A method of determining positioning of a sensor on a measurement site of a patient, said method comprising:
 determining a reference position of said measurement site within said sensor, which comprises calculating a first value from a first set of physiological signal data received from said sensor, wherein in said reference position said sensor is correctly positioned on said measurement site of said patient;
 determining whether a current position of said sensor is correctly positioned on said measurement site of said patient based, at least in part, on said reference position; and
 generating instructions for said patient for moving said sensor to said reference position when said sensor is not correctly positioned.

23. The method of claim 22, wherein determining whether said current position of said sensor is correctly positioned further comprises calculating a second value from a second set of physiological signal data received from said sensor.

24. The method of claim 22, wherein said current position is a spatially different position from said reference position in at least one direction.

25. A method of determining positioning of a sensor on a measurement site of a patient, said method comprising:
 determining a reference position of said measurement site within said sensor, wherein in said reference position said sensor is correctly positioned on said measurement site of said patient;
 determining whether a current position of said sensor is correctly positioned on said measurement site of said patient based, at least in part, on said reference position;
 generating instructions for said patient for moving said sensor to said reference position when said sensor is not correctly positioned; and
 updating said instructions until said sensor is positioned within a threshold value associated with said reference position.

* * * * *